United States Patent [19]

Bahr et al.

[11] Patent Number: 4,927,244
[45] Date of Patent: May 22, 1990

[54] USE OF COMPOUNDS OR MIXTURES OF COMPOUNDS WHICH HAVE A CHIRAL, ORTHOGONAL, MORE HIGHLY ORDERED SMECTIC PHASE IN THE RANGE OF SAID PHASE AS SWITCHING OR INDICATING MEDIUM

[75] Inventors: Christian Bahr; Gerd Heppke; Detlef Lötzsch, all of Berlin; Hans-Rolf Dübal, Königstein; Claus Escher, Mühltal; Dieter Ohlendorf, Liederbach, all of Fed. Rep. of Germany

[73] Assignee: Hoechst Aktiengesellschaft, Frankfurt am Main, Fed. Rep. of Germany

[21] Appl. No.: 177,685

[22] Filed: Apr. 5, 1988

[30] Foreign Application Priority Data

Apr. 7, 1987 [DE] Fed. Rep. of Germany ....... 3711360
May 29, 1987 [DE] Fed. Rep. of Germany ....... 3718174

[51] Int. Cl.$^5$ .............................................. G02F 1/13
[52] U.S. Cl. .............................. 350/350 S; 350/347 V; 350/347 E
[58] Field of Search ............. 350/350 S, 347 V, 347 E

[56] References Cited

U.S. PATENT DOCUMENTS

| | | | |
|---|---|---|---|
| 3,723,346 | 3/1973 | Taylor et al. | 350/350 S X |
| 4,139,273 | 2/1979 | Crossland et al. | 350/350 S X |
| 4,367,924 | 1/1983 | Clark et al. | 350/350 S X |
| 4,592,858 | 6/1986 | Higuchi et al. | 252/299.66 |
| 4,614,609 | 9/1986 | Inoue et al. | 350/350 S X |
| 4,638,073 | 1/1987 | Walba et al. | 252/299.61 |
| 4,647,398 | 3/1987 | Saito et al. | 350/350 S X |
| 4,695,651 | 9/1987 | Higuchi et al. | 252/299.66 |
| 4,714,323 | 12/1987 | Katagiri et al. | 350/350 S |
| 4,721,367 | 1/1988 | Yoshinaga et al. | 350/350 S |
| 4,722,594 | 2/1988 | Crossland et al. | 350/350 S |
| 4,728,458 | 5/1988 | Higuchi et al. | 252/299.65 |
| 4,729,847 | 3/1988 | Miyazawa et al. | 350/350 S X |
| 4,732,699 | 5/1988 | Higuchi et al. | 252/299.66 |
| 4,752,413 | 6/1988 | Inoue et al. | 350/350 S X |
| 4,775,223 | 10/1988 | Yoshinaga et al. | 252/299.68 |
| 4,813,771 | 3/1989 | Handschy et al. | 350/350 S |
| 4,838,663 | 6/1989 | Lagerwall et al. | 350/350 S |

FOREIGN PATENT DOCUMENTS

| | | | |
|---|---|---|---|
| 240385 | 10/1986 | German Democratic Rep. | 252/299.61 |
| 86/02937 | 5/1986 | World Int. Prop. O. | 252/299.66 |
| 86/02938 | 5/1986 | World Int. Prop. O. | 252/299.66 |
| 88/03525 | 5/1988 | World Int. Prop. O. | 252/299.61 |

OTHER PUBLICATIONS

Stephen Garoff and Robert B. Meyer, "Electroclinic Effect at the A-C Phase Change in a Chiral Smectic Liquid Crystal", Physical Review Letters, vol. 38, No. 15 (1977), pp. 848-851.

Garoff et al, Physical Review A, vol. 19(1), pp. 338-347 (Jan. 1979).

*Primary Examiner*—John Zazworsky
*Assistant Examiner*—Anita Pellman Gross
*Attorney, Agent, or Firm*—Curtis, Morris & Safford

[57] ABSTRACT

Use of compounds or mixtures of compounds which have a chiral, orthogonal, more highly ordered smectic phase in the range of said phase as switching or indicating medium.

Compounds which have a chiral, orthogonal, more highly ordered smectic phase, in particular an $S_B^*$ or an $S_E^*$ phase, can be used in the range of said phase or phases as indicating or switching medium in electro-optical indicating or switching components (devices) which are based on the exploitation of the electroclinic effect.

3 Claims, 1 Drawing Sheet

E = 0
DARK STATE

E < 0
BRIGHT STATE

E = 0
DARK STATE

E > 0
BRIGHT STATE

E < 0
BRIGHT STATE

USE OF COMPOUNDS OR MIXTURES OF COMPOUNDS WHICH HAVE A CHIRAL, ORTHOGONAL, MORE HIGHLY ORDERED SMECTIC PHASE IN THE RANGE OF SAID PHASE AS SWITCHING OR INDICATING MEDIUM

Use of compounds or mixtures of compounds which have a chiral, orthogonal, more highly ordered smectic phase in the range of said phase as switching or indicating medium.

BACKGROUND OF THE INVENTION

The unusual combination of anisotropic and fluid properties in liquid crystals have resulted in their use in a multiplicity of electro-optical switching and indicating devices. In these, their electrical, magnetic, elastic or thermal properties can be used for the purpose of orientation changes. Optical effects can then be achieved by means of their birefringence ("birefringence mode"), the intercalation of dichroically absorbing dyestuff molecules ("guest-host mode") or light scattering.

In this connection, the nematic phase (N) and the smectic high-temperature phases $S_A$ and $S_C$ or their chiral versions $N^*$, $S_A^*$ and $S_C^*$ have, apart from a few exceptions, hitherto been used.

The $S_A$ and $S_C$ phases have a layer structure with randomly distributed molecular centers of mass inside a layer. They are distinguished by the fact that in the $S_A$ phase the director $\hat{n}$ is perpendicular to the plane of the layer, i.e. parallel to the layer normal $\hat{z}$ (definition of the orthogonal phases), but in the $S_C$ phase a tilt is present which is specified by the angle $\theta$ between $\hat{n}$ and $\hat{z}$ (definition of the "tilted phases").

In the "bookshelf" geometry proposed by Clark and Lagerwall (N. A. Clark and S. T. Lagerwall, Appl. Phys. Lett. 36, 899 (1980)), the ferroelectricity of the $S_C^*$ phase can be exploited for the purpose of an electro-optical effect. This is based on the existence of two stable states between which a rapid switching takes place typically in 50 $\mu$s in an electric field of $10^7$ V/m (R. B. Meyer, L. Liebert, L. Strzlecki and P. Keller, I. Phys. (Paris) Letters 36, L-69 (1975)).

This ferroelectric effect is notable for an extremely non-linear electro-optical characteristic curve.

It is known that in the $S_A^*$ phase (chiral $S_A$ phase), a related, but linear process occurs which, following Garoff and Meyer (S. Garoff and R. B. Meyer, Phys. Rev. Lett. 38, 848 (1977)), is called the electroclinic effect. It is based on a field-induced angle of tilt $\theta$ in the per se orthogonal $S_A^*$ phase, which is proportional to the electric field E extending parallel to the smectic layers. The magnitude of the electroclinic effect is specified by the differential coefficient $(d\theta/dE)$. In the more highly ordered phases, for example $S_B$, $S_E$ etc., the molecular centers of mass are not randomly distributed inside a layer but are arranged regularly, like in a crystal lattice. This higher order is matched by a higher viscosity and solidity of the layers. The more highly ordered smectic phases, in particular the orthogonal $S_B$ and $S_E$ phases, were not therefore considered for use in electro-optical components in which rapid responses of the liquid-crystalline layers to changes in an applied electric field are required.

Surprisingly, it has now been found that $S_B^*$ (chiral $S_B$) phases and $S_E^*$ (chiral $S_E$) phases exhibit an electroclinic effect with unexpectedly short response times down to 1.5 $\mu$s, the electroclinic coefficient $d\theta/dE$ being, in addition, larger than in the $S_A^*$ phase.

SUMMARY OF THE INVENTION

The subject of the invention is therefore the use of compounds or mixtures of compounds which have a chiral, orthogonal, more highly ordered smectic phase, in particular an $S_B^*$ or an $S_E^*$ phase, in the range of said phase as indicating or switching medium in electro-optical indicating or switching components which are based on the electroclinic effect.

The subject of the invention is furthermore, in particular, the use of such compounds or mixtures of compounds in switching and indicating components (devices) from the group comprising (a) elliptical polarizers
(b) light modulators in "birefringence mode"
(c) light modulators in "guest-host mode"
(d) pulse chopper
(e) gray scales for display screens and printers
(f) electrically controlled matrices for nonlinear optical materials and
(g) sensors for electric fields, and switching and indicating components which contain the said compounds or mixtures of compounds.

As a result of the invention, a large number of compounds which were hitherto of only theoretical interest becomes available for use in electro-optical components. Thus, about 25% of the smectic substances listed in the tabular compilation entitled "Flüssige Kristalle in Tabellen", Demus et al., VEB Deutscher Verlag für Grundstoffindustrie, Leipzig 1974, have an $S_B$ or $S_E$ phase. If these are not chiral compounds, the chirality can be induced by adding chiral dopants.

BRIEF DESCRIPTION OF THE DRAWING

The following detailed description, given by way of example but not intended to limit the invention solely to the specific embodiment described, may best be understood in conjunction with the accompanying drawings, in which.

DESCRIPTION OF THE PREFERRED EMBODIMENTS

Figure 1:
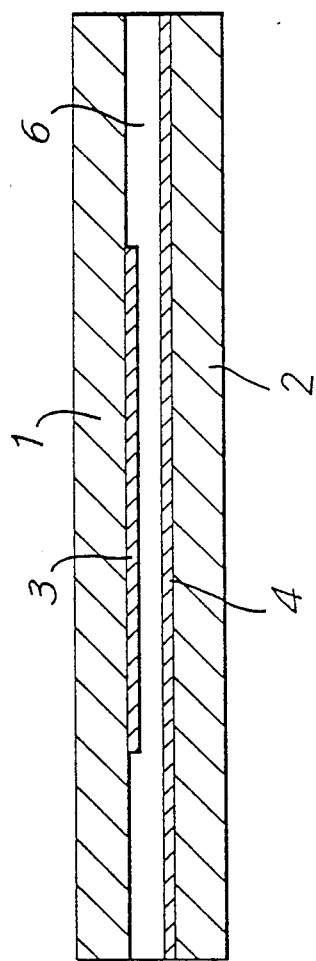
FIG. 1 schematically shows a cross section of a switching or indicating component which is based on the electroclinic effect.

The suitable compounds in the use according to the invention basically include those which are smectogenic, i.e. have a tendency to form smectic phases, and according to the invention this smectic phase of said compounds and mixtures of compounds must additionally be chiral, orthogonal and more highly ordered smectic. Examples of compounds of this type belong, in particular, to the compounds of the general formula (A):

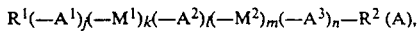

in which

R¹,R² denote, independently of each other, straight-chain or branched alkyl or alkenyl (with or without asymmetric carbon atom) containing 2 to 16 carbon atoms, it also being possible for one or two non-adjacent —CH₂-groups to be replaced by —O—, —S—, —CO—, —CO—O—, —O—CO— or —O—CO—O— and it also being possible for hydrogen to be replaced by fluorine, or one of the following radicals

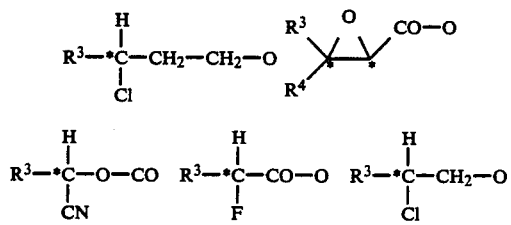

A¹,A²,A³ denote, independently of each other, 1,4-phenylene, trans-1,4-cyclohexylene, pyrazine-2,5-diyl, pyridazine-3,6-diyl, pyridine-2,5-diyl, pyrimidine-2,5-diyl, 1,3,4-thiadiazole-2,5-diyl, M¹,M² denote, independently of each other, CO—O, O—CO, CO—S, S—CO, CH₂O, OCH₂, CH=N, N=CH, CH₂—CH₂, N=N, N=N(O), R³,R⁴ denote, independently of each other, hydrogen or straight-chain or branched alkyl containing 1 to 16 or alkenyl containing 2 to 16 carbon atoms in which it is also possible for a —CH₂— group to be replaced by —O—, —CO—O— or —O—CO—, j,k,l,m,n denote 0 or 1, where j+l+n=2 or 3.

The compounds are known to those skilled in the field of liquid crystals from the literature (see, for example, above tabular compilation) or are described for the first time in DE-A-3,718,174 (for the oxirane derivatives).

The electroclinic effect in more highly ordered smectic phases is illustrated both on the basis of two optically active individual compounds, namely

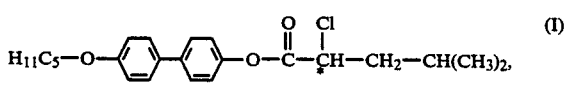

phase sequence: K* 58 $S_E^*$ 63,5 $S_B^*$ 72,5 $S_A^*$ 75 I*

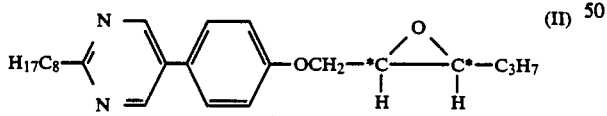

phase sequence: K* 55 $S_B^*$ 90 $S_A^*$ 102 I*, and on the basis of some mixtures. To measure the characteristic parameters, a measuring cell was used which had a path length of 2 μm in the substance to be measured. The planar orientation ("bookshelf" geometry) was obtained by shearing and/or orientation layers. The structure of the measuring cell has been described for ferroelectric liquid crystal layers by Skarp and Andersson (K. Skarp and G. Andersson, Ferroelectrics Letters 6, 67 (1986)).

The electroclinic coefficient dθ/dE was measured by applying a DC voltage and optically determining the angle of tilt θ between crossed polarizing filters on the basis of the dark position relative to the zero-field position in the polarization microscope.

The electroclinic switching time was determined by determining the cutoff frequency $f_G$, up to which the reorientation of the molecules can still follow the alternating field, on the basis of the frequency dependency of the dielectric constants. The reciprocal of said frequency is the minimum electroclinic switching time.

The measured values obtained with the compounds (I) and (II) are shown in Tables I and II and the mixture results in Table III. In the case of compound (I) it is evident that the electroclinic coefficient dθ/dE is significantly greater in the more highly ordered $S_E$ or $S_B$ phases than in the $S_A^*$ phase. In the case of compound (II), no measurable electroclinic effect was found in the $S_A^*$ phase.

The mixture example M1 shows how the electroclinic effect can be very much increased by suitable dopants.

TABLE 1

Measured values for the compound (I)

| t (°C.) | Phase | $\frac{d\theta}{dE}$ ($10^{-9}$ rad m/V) | θ at $10^7$ V/m (degree) | $f_G$ (KHz) |
|---|---|---|---|---|
| 62.5 | $S_E^*$ | 5.0 | 2.8 | 2.5 |
| 64.3 | $S_B^*$ | 7.0 | 4.0 | 36 |
| 70.5 | $S_B^*$ | 5.3 | 3.0 | 230 |
| 72.1 | $S_B^*$ | 5.2 | 3.0 | 630 |
| 72.5 | $S_A^*$ | 3.8 | 2.2 | >3000 |

TABLE 2

Measured values for the compound (II)

| t (°C.) | Phase | $\frac{d\theta}{dE}$ ($10^{-9}$ rad m/V) | θ at $10^7$ V/m (degree) |
|---|---|---|---|
| 60 | $S_B^*$ | 2.0 | 1.2 |
| 70 | $S_B^*$ | 1.6 | 1.0 |
| 80 | $S_B^*$ | 1.1 | 0.6 |
| 95 | $S_A^*$ | | |
| 100 | $S_A^*$ | No electroclinic effect observed | |

TABLE 3

Measured values for the mixtures

| Mixture | Phase | t (°C.) | $\frac{d\theta}{dE}$ ($10^{-9}$ rad m/V) | θ at $10^7$ V/m (degree) |
|---|---|---|---|---|
| M1 (a) | $S_A^*$ | 72 | No electroclinic effect observed. | |
| | $S_B^*$ | 69 | Electroclinic effect detected optically | |
| | $S_B^*$ | 60 | 0.9 | 0.5 |
| | $S_B^*$ | 50 | 1.4 | 0.8 |
| | $S_B^*$ | 40 | 2.3 | 1.3 |
| | $S_B^*$ | 36 | 3.5 | 2.0 |
| M2 (b) | $S_B^*$ | 50 | 0.6 | 0.35 |
| M3 (c) | $S_B^*$ | 40 | 1.8 | 1.0 |
| | $S_B^*$ | 35 | 1.9 | 1.1 |

TABLE 3-continued

| | | Measured values for the mixtures | | |
|---|---|---|---|---|
| Mixture | Phase | t (°C.) | $\frac{d\theta}{dE}$ ($10^{-9}$ rad m/V) | $\theta$ at $10^7$ V/m (degree) |
| | $S_B^*$ | 30 | 2.0 | 1.1 |

Footnotes
(a) M1
Binary mixture of substance II (x = 0.85) with the substance (see DE-A-3,718,174) III:

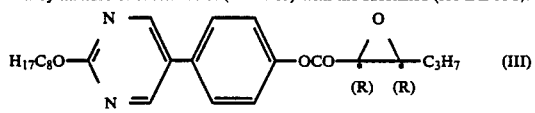

(mole fraction x = 0.15).
Phase sequence of the mixture: K 40 (supercold 32) $S_B^*$ 68 $S_A^*$ 75-90 I
(b) M2
Binary mixtuer of IV(x = 0.88) and the dopant V (x = 0.12):

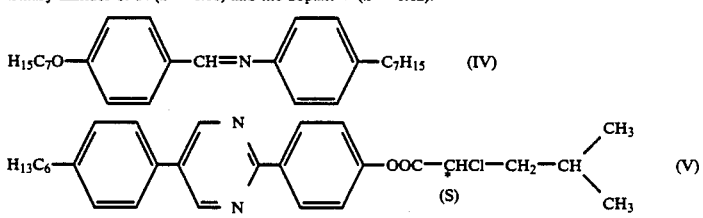

Clearing point of the mixture: 95° C.
(c) M3
Binary mixture of IV (x = 0.72) and the dopant VI (x = 0.28):

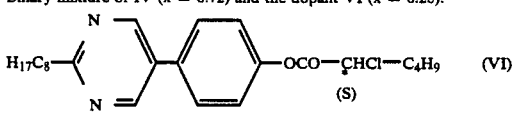

Clearing point of the mixture: 66° C.
For the field strength used of up to $4.10^7$ V/m the angle of tilt $\theta$ was strictly proportional to the field strength both in the $S_B^*$ and in the $S_E^*$ phase.

In the practical utilization of the electroclinic effect, known techniques may be resorted to. Thus the field-dependent orientation of the director n can be exploited together with the optical anisotropy (birefringence).

Figure 2A:
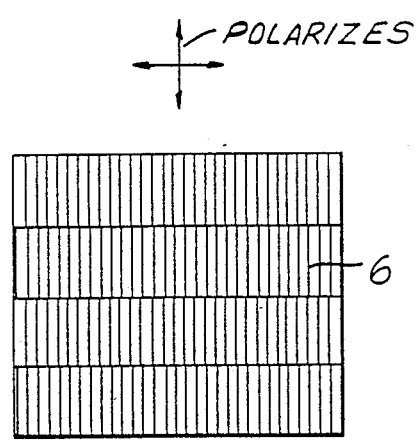
FIG. 2a is a schematic topview representation of an undistorted geometry for a planarly oriented $S_B^*$ or $S_E^*$ phase when no field is applied.
Figure 2B:
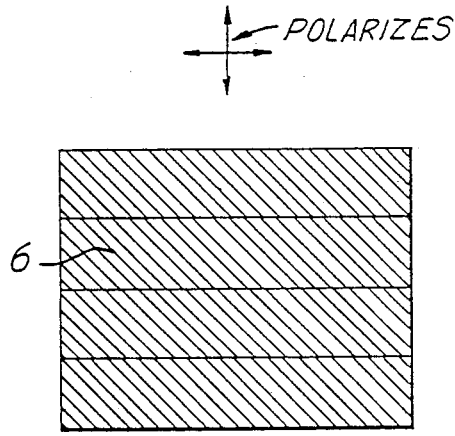
FIG. 2b is a schematic topview representation of a first embodiment of a field-induced tilted geometry for a planarly oriented $S_B^*$ or $S_E^*$ phase.
Figure 2C:
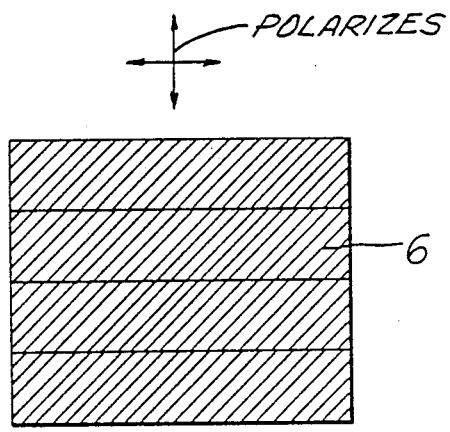
FIG. 2c is a schematic topview representation of a second embodiment of a field-induced tilted geometry for a planarly oriented $S_B^*$ or $S_E^*$ phase.

Referring now to FIG. 1, the component consists of a planarly oriented $S_B^*$ or $S_E^*$ phase 6 which is situated between two transparent electrodes 3 and 4 and two crossed polarizers 1 and 2. Provided no field is applied, the director ñ is parallel to one of the polarizers and no light passes through the second polarizer as shown in FIG. 2a. If a field is applied, the director ñ tilts, the birefringence becomes operative and the component becomes transparent as shown in FIGS. 2b and 2c.

There are 2 possibilities for constructing different switching and indicating components:

a. Elliptical polarizer

In this effect, the birefringence of the liquid crystal is exploited. If linearly polarized light is incident on a cell as described above which, however, must not be fitted with polarizers, then the light leaves the cell elliptically polarized. Special cases are circularly or again linearly polarized emergent light. The ellipticity can then be continuously controlled by the electroclinic effect.

b. Light modulator ("birefringence mode")

Using polarizers, the case described under (a.) can be used for light modulation, i.e. to generate electrically controlled variations in intensity. We have already been able to use the cell described above as a light modulator.

If polarizers which are not crossed are used, but a variable angle $\Psi$ is introduced between polarizer and analyzer, then the following is obtained for the emergent intensity I ($I_o$ is the light intensity incident through the polarizer):

$$I(E) = I_o[\cos^2 \Psi + \sin 4\theta(E)\cdot\sin 2(\Psi - 2\theta(E))\cdot\sin^2 (\pi \Delta nd/\lambda)]$$

$\theta(E)$ is the field-induced tilt, d is the cell thickness, $\Delta n = n - n$ is the optical anisotropy, and $\lambda$ is the wavelength of the light in vacuo.

The above equation results in various modulators in which equal (symmetrical mode) or different brightnesses (unsymmetrical mode) are associated with the extreme field strengths ($+E_{max}$ or $-E_{max}$).

An advantage of the higher sensitivity ($d\theta/dE$) of the more highly ordered smectic phases is an increased CMOS ($\pm 15$ V) compatibility.

c. Light modulator ("guest-host mode")

The light modulator can be constructed also by means of intercalation of dichroically absorbing molecules. This makes one of the two polarizers superfluous. As a result of applying an electric field, the absorber can be reoriented together with the liquid-crystalline phase and, consequently, the absorption axis can be rotated. The absorber may also contain IR chromophores.

d. Pulse chopper

The electro-optical components described under (a.)-(c.) may also be used to generate light pulses of any shape which do not repeat with time.

For this purposes, a freely programable pulse generator, for example, can be connected to a cell as described above and, using continuous-wave light sources, such as CW lasers, any desired pulses may be chopped.

e. Generation of a gray scale

The linear coupling of the angle of tilt $\theta$ to the field E makes it possible to generate a continuous gray scale for display screens, printers and the like.

The mode of operation of this unit is as under (a.)-(c.) with the difference that a component with many small electrodes (so-called "pixels") is involved which together form a gray screen.

f. Electrically alignable phases as matrices for non-linear optical materials It has been known for some time that a number of organic compounds have very large non-linear optical coefficients (I. Zyss, J. Mol. Electron. 1, 25 (1985)).

The main problem in using them is in the alignment which can be carried out either by growing single crystals, by the Langmuir-Blodgett technique or by embedding in liquid crystal matrices.

The electroclinic effect in LC phases of high optical quality can be used for the electrically controlled fine matching of said materials (for example "phase matching" in frequency multiplication).

g. Sensors for electric fields

The electroclinic effect can be exploited for detecting an unknown electric field. Such a field sensor consists of two glass plates without electrodes between which a planarly oriented $S_B^*$ or $S_E^*$ liquid crystal is situated. If said sensor is now brought into an electric field, the magnitude and direction of the field can be detected by means of the electroclinic effect by placing the cell between crossed polarizers or else using the "guest-host" mode. For such applications, high sensitivity ($d\theta/dE$) is necessary, such as has been found here in the more highly ordered phases.

We claim:

1. A switching or indicating component which is based on the electroclinic effect, comprising as switching or indicating medium a compound or a mixture of compounds which are present in a chiral, orthogonal, more highly ordered smectic phase in the operational state of the switching or indicating component.

2. The switching or indicating component as claimed in claim 1, wherein the phase is an $S_B^*$ or $S_E^*$ phase.

3. The switching or indicating component as claimed in claim 1 selected from the group consisting of
   (a) elliptical polarizers
   (b) light modulators in "birefringence mode"
   (c) light modulators in "guest-host mode"
   (d) pulse chopper
   (e) gray scales for display screens and printers
   (f) electrically controlled matrices for non-linear optical materials and
   (g) sensors for electric fields.